US012708436B2

(12) United States Patent
Rodriguez Soto

(10) Patent No.: US 12,708,436 B2
(45) Date of Patent: Aug. 18, 2026

(54) MULTI-ELECTRODE CATHETER WITH INTERLACED SUBSTRATE

(71) Applicant: Biosense Webster (Israel) Ltd., Yokneam (IL)

(72) Inventor: Juan Rodriguez Soto, Irvine, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 255 days.

(21) Appl. No.: 18/508,429

(22) Filed: Nov. 14, 2023

(65) Prior Publication Data

US 2024/0216050 A1 Jul. 4, 2024

Related U.S. Application Data

(60) Provisional application No. 63/477,673, filed on Dec. 29, 2022.

(51) Int. Cl.
*A61B 18/14* (2006.01)
*A61B 18/00* (2006.01)

(52) U.S. Cl.
CPC .. *A61B 18/1492* (2013.01); *A61B 2018/0016* (2013.01); *A61B 2018/00267* (2013.01); *A61B 2018/00577* (2013.01)

(58) Field of Classification Search
CPC ........... A61B 2018/00577; A61B 2018/00642; A61B 2018/00654; A61B 2018/0066; A61B 2018/00672; A61B 2018/00678; A61B 2018/00708; A61B 2018/00779; A61B 2018/00791; A61B 2018/00875; A61B 2018/1823; A61B 2018/1869
See application file for complete search history.

(56) References Cited

U.S. PATENT DOCUMENTS

| | | | |
|---|---|---|---|
| 4,699,147 | A | 10/1987 | Chilson et al. |
| 4,940,064 | A | 7/1990 | Desai |
| 5,215,103 | A | 6/1993 | Desai |
| 5,255,679 | A | 10/1993 | Imran |
| 5,293,869 | A | 3/1994 | Edwards et al. |
| 5,309,910 | A | 5/1994 | Edwards et al. |
| 5,324,284 | A | 6/1994 | Imran |
| 5,345,936 | A | 9/1994 | Pomeranz et al. |

(Continued)

FOREIGN PATENT DOCUMENTS

| | | | |
|---|---|---|---|
| CN | 102665586 | A | 9/2012 |
| CN | 102892453 | A | 1/2013 |

(Continued)

OTHER PUBLICATIONS

Extended European Search Report for European Application No. 20172013.3, mailed Sep. 21, 2020, 8 Pages.

(Continued)

*Primary Examiner* — Tigist S Demie

(57) ABSTRACT

Catheters are presented herein having at least one electrode pair with a first electrode in the pair configured to contact tissue to receive and/or apply electrical signals for mapping and/or ablation and a second electrode in the pair being positioned facing an opposite direction, away from the tissue, and configured to function as a reference electrode for the first electrode. The first and second electrodes are positioned on separate substrates that are interwoven with each other.

17 Claims, 5 Drawing Sheets

(56) References Cited

U.S. PATENT DOCUMENTS 5,365,926 A 11/1994 Desai
5,391,199 A 2/1995 Ben-Haim
5,396,887 A 3/1995 Imran
5,400,783 A 3/1995 Pomeranz et al.
5,411,025 A 5/1995 Webster, Jr.
5,415,166 A 5/1995 Imran
5,443,489 A 8/1995 Ben-Haim
5,456,254 A 10/1995 Pietroski et al.
5,465,717 A 11/1995 Imran et al.
5,476,495 A 12/1995 Kordis et al.
5,499,981 A 3/1996 Kordis
5,526,810 A 6/1996 Wang
5,546,940 A 8/1996 Panescu et al.
5,549,108 A 8/1996 Edwards et al.
5,558,073 A 9/1996 Pomeranz et al.
5,558,091 A 9/1996 Acker et al.
5,577,509 A 11/1996 Panescu et al.
5,595,183 A 1/1997 Swanson et al.
5,598,848 A 2/1997 Swanson et al.
5,609,157 A 3/1997 Panescu et al.
5,628,313 A 5/1997 Webster, Jr.
5,630,918 A 5/1997 Takahara et al.
5,681,280 A 10/1997 Rusk et al.
5,702,438 A 12/1997 Avitall
5,722,401 A 3/1998 Pietroski et al.
5,722,403 A 3/1998 McGee et al.
5,725,525 A 3/1998 Kordis
5,730,128 A 3/1998 Pomeranz et al.
5,738,096 A 4/1998 Ben-Haim
5,782,899 A 7/1998 Imran
5,881,727 A 3/1999 Edwards
5,893,847 A 4/1999 Kordis
5,904,680 A 5/1999 Kordis et al.
5,911,739 A 6/1999 Kordis et al.
5,928,228 A 7/1999 Kordis et al.
5,944,022 A 8/1999 Nardella et al.
5,964,757 A 10/1999 Ponzi
5,968,040 A 10/1999 Swanson et al.
5,983,126 A 11/1999 Wittkampf
6,014,579 A 1/2000 Pomeranz et al.
6,014,590 A 1/2000 Whayne et al.
6,071,280 A 6/2000 Edwards et al.
6,071,282 A 6/2000 Fleischman
6,119,030 A 9/2000 Morency
6,123,699 A 9/2000 Webster, Jr.
6,142,993 A 11/2000 Whayne et al.
6,171,277 B1 1/2001 Ponzi
6,172,499 B1 1/2001 Ashe
6,183,435 B1 2/2001 Bumbalough et al.
6,183,463 B1 2/2001 Webster, Jr.
6,198,974 B1 3/2001 Webster, Jr.
6,210,407 B1 4/2001 Webster
6,216,043 B1 4/2001 Swanson et al.
6,216,044 B1 4/2001 Kordis
6,239,724 B1 5/2001 Doron et al.
6,245,068 B1 6/2001 Olson et al.
6,267,746 B1 7/2001 Bumbalough
6,332,089 B1 12/2001 Acker et al.
6,415,187 B1 7/2002 Kuzma et al.
6,428,537 B1 8/2002 Swanson et al.
6,445,864 B2 9/2002 Jiang et al.
6,484,118 B1 11/2002 Govari
6,522,932 B1 2/2003 Kuzma et al.
6,574,492 B1 6/2003 Ben-Haim et al.
6,584,345 B2 6/2003 Govari
6,590,963 B2 7/2003 Mohammadian et al.
6,600,948 B2 7/2003 Ben-Haim et al.
6,618,612 B1 9/2003 Acker et al.
6,658,302 B1 12/2003 Kuzma et al.
6,690,963 B2 2/2004 Ben-Haim
6,738,655 B1 5/2004 Sen et al.
6,741,878 B2 5/2004 Fuimaono et al.
6,748,255 B2 6/2004 Fuimaono et al.
6,780,183 B2 8/2004 Jimenez, Jr. et al.
6,788,967 B2 9/2004 Ben-Haim et al.
6,837,886 B2 1/2005 Collins et al.
6,866,662 B2 3/2005 Fuimaono et al.
6,892,091 B1 5/2005 Ben-Haim
6,970,730 B2 11/2005 Fuimaono et al.
6,973,340 B2 12/2005 Fuimaono et al.
6,980,858 B2 12/2005 Fuimaono et al.
7,048,734 B1 5/2006 Fleischman et al.
7,099,712 B2 8/2006 Fuimaono et al.
7,149,563 B2 12/2006 Fuimaono et al.
7,155,270 B2 12/2006 Solis et al.
7,255,695 B2 8/2007 Falwell et al.
7,257,434 B2 8/2007 Fuimaono et al.
7,257,435 B2 8/2007 Plaza
7,366,557 B2 4/2008 Bautista
7,399,299 B2 7/2008 Daniel et al.
7,412,274 B2 8/2008 Mejia
7,429,261 B2 9/2008 Kunis et al.
7,522,950 B2 4/2009 Fuimaono et al.
7,536,218 B2 5/2009 Govari et al.
RE41,334 E 5/2010 Beatty et al.
7,756,567 B2 7/2010 Kuduvalli et al.
7,756,576 B2 7/2010 Levin
7,846,157 B2 12/2010 Kozel
7,848,757 B2 12/2010 Duggi et al.
7,848,787 B2 12/2010 Osadchy
7,869,865 B2 1/2011 Govari et al.
7,930,018 B2 4/2011 Harlev et al.
8,007,495 B2 8/2011 McDaniel et al.
8,048,063 B2 11/2011 Aeby et al.
8,103,327 B2 1/2012 Harlev et al.
8,167,845 B2 5/2012 Wang et al.
8,206,404 B2 6/2012 De La Rama et al.
8,224,416 B2 7/2012 De La Rama et al.
8,235,988 B2 8/2012 Davis et al.
8,271,099 B1 9/2012 Swanson
8,273,084 B2 9/2012 Kunis et al.
8,346,339 B2 1/2013 Kordis et al.
8,391,947 B2 3/2013 Urman et al.
8,435,232 B2 5/2013 Aeby et al.
8,447,377 B2 5/2013 Harlev et al.
8,456,182 B2 6/2013 Bar-Tal et al.
8,480,669 B2 7/2013 Pappone et al.
8,498,686 B2 7/2013 Grunewald
8,517,999 B2 8/2013 Pappone et al.
8,545,490 B2 10/2013 Mihajlovic et al.
8,560,086 B2 10/2013 Just et al.
8,565,851 B2 10/2013 Lau et al.
8,567,265 B2 10/2013 Aeby et al.
8,571,626 B2 10/2013 Lau et al.
8,603,069 B2 12/2013 Selkee
8,712,550 B2 4/2014 Grunewald
8,715,279 B2 5/2014 De La Rama et al.
8,734,440 B2 5/2014 Wu
8,744,599 B2 6/2014 Tegg
8,755,861 B2 6/2014 Harlev et al.
8,764,742 B2 7/2014 Pappone et al.
8,790,341 B2 7/2014 Pappone et al.
8,825,130 B2 9/2014 Just et al.
8,827,910 B2 9/2014 De La Rama et al.
8,906,011 B2 12/2014 Gelbart et al.
8,945,120 B2 2/2015 McDaniel et al.
8,956,353 B2 2/2015 Govari et al.
8,974,454 B2 3/2015 De La Rama et al.
8,979,837 B2 3/2015 De La Rama et al.
8,979,839 B2 3/2015 De La Rama et al.
9,037,264 B2 5/2015 Just et al.
9,044,245 B2 6/2015 Condie et al.
9,131,980 B2 9/2015 Bloom
9,204,929 B2 12/2015 Solis
9,277,960 B2 3/2016 Weinkam et al.
9,314,208 B1 4/2016 Altmann et al.
9,480,416 B2 11/2016 Govari et al.
9,480,491 B1 11/2016 Dostal et al.
9,486,282 B2 11/2016 Solis
9,554,718 B2 1/2017 Bar-Tal et al.
9,561,075 B2 2/2017 Pappone et al.
D782,686 S 3/2017 Werneth et al.
9,585,588 B2 3/2017 Marecki et al.
9,597,036 B2 3/2017 Aeby et al.

(56) References Cited

U.S. PATENT DOCUMENTS 9,616,199 B2 4/2017 Wang et al.
9,642,675 B2 5/2017 Werneth et al.
9,687,297 B2 6/2017 Just et al.
9,693,733 B2 7/2017 Altmann et al.
9,724,492 B2 8/2017 De La Rama et al.
9,782,099 B2 10/2017 Williams et al.
9,788,895 B2 10/2017 Solis
9,801,585 B2 10/2017 Shah et al.
9,801,681 B2 10/2017 Laske et al.
9,814,618 B2 11/2017 Nguyen et al.
9,820,664 B2 11/2017 Hoitink et al.
9,833,161 B2 12/2017 Govari
9,833,608 B2 12/2017 Masson
9,848,795 B2 12/2017 Marecki et al.
9,877,781 B2 1/2018 Grasse et al.
9,894,756 B2 2/2018 Weinkam et al.
9,895,073 B2 2/2018 Solis
9,907,480 B2 3/2018 Basu et al.
9,907,609 B2 3/2018 Cao et al.
9,949,656 B2 4/2018 Wu et al.
9,962,224 B2 5/2018 Pappone et al.
9,974,460 B2 5/2018 Wu et al.
9,986,949 B2 6/2018 Govari et al.
9,993,160 B2 6/2018 Salvestro et al.
10,014,607 B1 7/2018 Govari et al.
10,028,376 B2 7/2018 Weinkam et al.
10,034,637 B2 7/2018 Harlev et al.
10,039,494 B2 8/2018 Altmann et al.
10,039,598 B2 8/2018 De La Rama et al.
10,045,707 B2 8/2018 Govari
10,078,713 B2 9/2018 Auerbach et al.
10,111,623 B2 10/2018 Jung et al.
10,130,420 B2 11/2018 Basu et al.
10,130,422 B2 11/2018 Ditter
10,136,828 B2 11/2018 Houben et al.
10,143,394 B2 12/2018 Solis
10,172,536 B2 1/2019 Maskara et al.
10,182,762 B2 1/2019 Just et al.
10,194,818 B2 2/2019 Williams et al.
10,201,311 B2 2/2019 Chou et al.
10,219,860 B2 3/2019 Harlev et al.
10,219,861 B2 3/2019 Just et al.
10,220,187 B2 3/2019 De La Rama et al.
10,231,328 B2 3/2019 Weinkam et al.
10,238,309 B2 3/2019 Bar-Tal et al.
10,278,590 B2 5/2019 Salvestro et al.
D851,774 S 6/2019 Werneth et al.
10,314,505 B2 6/2019 Williams et al.
10,314,507 B2 6/2019 Govari et al.
10,314,648 B2 6/2019 Ge et al.
10,314,649 B2 6/2019 Bakos et al.
10,349,855 B2 7/2019 Zeidan et al.
10,350,003 B2 7/2019 Weinkam et al.
10,362,991 B2 7/2019 Tran et al.
10,375,827 B2 8/2019 Weinkam et al.
10,376,170 B2 8/2019 Quinn et al.
10,376,221 B2 8/2019 Iyun et al.
10,398,348 B2 9/2019 Osadchy et al.
10,403,053 B2 9/2019 Katz et al.
10,433,903 B2 10/2019 Pappone et al.
10,441,188 B2 10/2019 Katz et al.
10,470,682 B2 11/2019 Deno et al.
10,470,714 B2 11/2019 Altmann et al.
10,482,198 B2 11/2019 Auerbach et al.
10,492,729 B2 12/2019 De La Rama et al.
10,492,857 B2 12/2019 Guggenberger et al.
10,537,259 B2 1/2020 Wu et al.
10,542,620 B2 1/2020 Weinkam et al.
10,575,743 B2 3/2020 Basu et al.
10,575,745 B2 3/2020 Solis
10,576,244 B2 3/2020 De La Rama et al.
10,582,871 B2 3/2020 Williams et al.
10,582,894 B2 3/2020 Ben Zrihem et al.
10,596,346 B2 3/2020 Aeby et al.
10,602,947 B2 3/2020 Govari et al.
10,617,867 B2 4/2020 Viswanathan et al.
10,660,700 B2 5/2020 Beeckler et al.
10,660,702 B2 5/2020 Viswanathan et al.
10,667,753 B2 6/2020 Werneth et al.
10,674,929 B2 6/2020 Houben et al.
10,681,805 B2 6/2020 Weinkam et al.
10,682,181 B2 6/2020 Cohen et al.
10,687,892 B2 6/2020 Long et al.
10,702,177 B2 7/2020 Aujla
10,702,178 B2 7/2020 Dahlen et al.
10,716,477 B2 7/2020 Salvestro et al.
10,758,304 B2 9/2020 Aujla
10,765,371 B2 9/2020 Hayam et al.
10,772,566 B2 9/2020 Aujila
10,799,281 B2 10/2020 Goertzen et al.
10,842,558 B2 11/2020 Harlev et al.
10,842,561 B2 11/2020 Viswanathan et al.
10,842,990 B2 11/2020 De La Rama et al.
10,857,349 B2 12/2020 De La Rama et al.
10,863,914 B2 12/2020 Govari et al.
10,881,376 B2 1/2021 Shemesh et al.
10,898,139 B2 1/2021 Guta et al.
10,905,329 B2 2/2021 Bar-Tal et al.
10,912,484 B2 2/2021 Ziv-Ari et al.
10,918,306 B2 2/2021 Govari et al.
10,939,871 B2 3/2021 Altmann et al.
10,952,795 B2 3/2021 Cohen et al.
10,973,426 B2 4/2021 Williams et al.
10,973,461 B2 4/2021 Baram et al.
10,987,045 B2 4/2021 Basu et al.
11,006,902 B1 5/2021 Bonyak et al.
11,040,208 B1 6/2021 Govari et al.
11,045,628 B2 6/2021 Beeckler et al.
11,051,877 B2 7/2021 Sliwa et al.
11,109,788 B2 9/2021 Rottmann et al.
11,116,435 B2 9/2021 Urman et al.
11,129,574 B2 9/2021 Cohen et al.
11,160,482 B2 11/2021 Solis
11,164,371 B2 11/2021 Yellin et al.
2001/0001314 A1 5/2001 Davison et al.
2003/0236455 A1 12/2003 Swanson et al.
2004/0199200 A1 10/2004 Teague et al.
2004/0210121 A1 10/2004 Fuimaono et al.
2004/0254572 A1 12/2004 McIntyre et al.
2005/0159741 A1 7/2005 Paul et al.
2006/0100669 A1 5/2006 Fuimaono et al.
2007/0093806 A1 4/2007 Desai et al.
2007/0255273 A1 11/2007 Fernandez et al.
2007/0276212 A1 11/2007 Fuimaono et al.
2008/0249463 A1 10/2008 Pappone et al.
2008/0249522 A1 10/2008 Pappone et al.
2008/0281391 A1 11/2008 MacAdam et al.
2008/0294158 A1 11/2008 Pappone et al.
2009/0012517 A1 1/2009 De La Rama et al.
2009/0198300 A1 8/2009 Zhang et al.
2010/0152731 A1 6/2010 De La Rama et al.
2010/0174177 A1 7/2010 Wu
2010/0286684 A1 11/2010 Hata et al.
2011/0118726 A1 5/2011 De La Rama et al.
2011/0160574 A1 6/2011 Harlev et al.
2011/0190625 A1 8/2011 Harlev et al.
2011/0245756 A1 10/2011 Arora et al.
2011/0288392 A1 11/2011 De La Rama et al.
2011/0301597 A1 12/2011 McDaniel et al.
2011/0313417 A1 12/2011 De La Rama et al.
2012/0010490 A1 1/2012 Kauphusman et al.
2012/0130217 A1 5/2012 Kauphusman et al.
2012/0130218 A1 5/2012 Kauphusman et al.
2012/0172859 A1 7/2012 Condie et al.
2012/0239031 A1 9/2012 Pappone et al.
2012/0265130 A1 10/2012 De La Rama et al.
2012/0296232 A1 11/2012 Ng
2013/0030426 A1 1/2013 Gallardo et al.
2013/0085479 A1 4/2013 De La Rama et al.
2013/0090651 A1 4/2013 Smith
2013/0172872 A1 7/2013 Subramaniam et al.
2013/0172883 A1 7/2013 Lopes et al.
2013/0178850 A1 7/2013 Lopes et al.
2013/0190587 A1 7/2013 Lopes et al.

(56) References Cited

U.S. PATENT DOCUMENTS

2013/0226167 A1 8/2013 Kaplan et al.
2013/0253504 A1 9/2013 Fang
2013/0274582 A1 10/2013 Afonso et al.
2013/0296852 A1 11/2013 Madjarov et al.
2013/0310825 A1 11/2013 Pappone et al.
2013/0338467 A1 12/2013 Grasse et al.
2014/0025069 A1 1/2014 Willard et al.
2014/0052118 A1 2/2014 Laske et al.
2014/0180147 A1 6/2014 Thakur et al.
2014/0180151 A1 6/2014 Maskara et al.
2014/0180152 A1 6/2014 Maskara et al.
2014/0194716 A1 7/2014 Diep et al.
2014/0200639 A1 7/2014 De La Rama
2014/0207136 A1 7/2014 De La Rama et al.
2014/0257069 A1 9/2014 Eliason et al.
2014/0276712 A1 9/2014 Mallin et al.
2014/0296902 A1 10/2014 Huszar et al.
2014/0303619 A1 10/2014 Pappone et al.
2014/0309512 A1 10/2014 Govari et al.
2014/0316294 A1 10/2014 Maskara et al.
2014/0316496 A1 10/2014 Masson et al.
2014/0330269 A1 11/2014 Pappone et al.
2014/0343546 A1 11/2014 De La Rama et al.
2015/0011991 A1 1/2015 Buysman et al.
2015/0045863 A1 2/2015 Litscher et al.
2015/0105645 A1 4/2015 Subramaniam et al.
2015/0105770 A1 4/2015 Amit
2015/0119878 A1 4/2015 Heisel et al.
2015/0133919 A1 5/2015 McDaniel et al.
2015/0208942 A1 7/2015 Bar-Tal et al.
2015/0209547 A1 7/2015 De La Rama et al.
2015/0250424 A1 9/2015 Govari et al.
2015/0270634 A1 9/2015 Buesseler et al.
2015/0342532 A1 12/2015 Basu et al.
2015/0351652 A1 12/2015 Marecki et al.
2015/0374252 A1 12/2015 De La Rama et al.
2016/0073913 A1 3/2016 Francis et al.
2016/0081746 A1 3/2016 Solis
2016/0113709 A1 4/2016 Maor
2016/0143588 A1 5/2016 Hoitink et al.
2016/0183877 A1 6/2016 Williams et al.
2016/0213916 A1 7/2016 De La Rama
2016/0228023 A1 8/2016 Govari
2016/0228062 A1 8/2016 Altmann et al.
2016/0242667 A1 8/2016 Fay et al.
2016/0278853 A1 9/2016 Ogle et al.
2016/0302858 A1 10/2016 Bencini
2016/0317093 A1 11/2016 Berenfeld et al.
2016/0338770 A1 11/2016 Bar-Tal et al.
2016/0346038 A1 12/2016 Helgeson et al.
2016/0374753 A1 12/2016 Wu et al.
2017/0000365 A1 1/2017 Wu et al.
2017/0007158 A1 1/2017 Gross et al.
2017/0027638 A1 2/2017 Solis
2017/0035497 A1 2/2017 Nagale et al.
2017/0042449 A1 2/2017 Deno et al.
2017/0049348 A1 2/2017 Deno et al.
2017/0049349 A1 2/2017 Sallee et al.
2017/0065227 A1 3/2017 Marrs et al.
2017/0065341 A1 3/2017 Pappone et al.
2017/0071494 A1 3/2017 Solis et al.
2017/0071543 A1 3/2017 Basu et al.
2017/0071544 A1 3/2017 Basu et al.
2017/0071665 A1 3/2017 Solis
2017/0095173 A1 4/2017 Bar-Tal et al.
2017/0100187 A1 4/2017 Basu et al.
2017/0105796 A1 4/2017 Pappone et al.
2017/0112404 A1 4/2017 De La Rama et al.
2017/0112405 A1 4/2017 Sterrett et al.
2017/0143227 A1 5/2017 Marecki et al.
2017/0156790 A1 6/2017 Aujla
2017/0165000 A1 6/2017 Basu et al.
2017/0185702 A1 6/2017 Auerbach et al.
2017/0202515 A1 7/2017 Zrihem et al.
2017/0221262 A1 8/2017 Laughner et al.
2017/0224958 A1 8/2017 Cummings et al.
2017/0251978 A1 9/2017 Rodrigo Bort et al.
2017/0265812 A1 9/2017 Williams et al.
2017/0273738 A1 9/2017 Wu
2017/0281031 A1 10/2017 Houben et al.
2017/0281268 A1 10/2017 Tran et al.
2017/0296125 A1 10/2017 Altmann et al.
2017/0296251 A1 10/2017 Wu et al.
2017/0319269 A1 11/2017 Oliverius et al.
2017/0332970 A1 11/2017 Aujla
2017/0347959 A1 12/2017 Guta et al.
2017/0354338 A1 12/2017 Levin et al.
2017/0354339 A1 12/2017 Zeidan et al.
2017/0354364 A1 12/2017 Bar-Tal et al.
2017/0354797 A1 12/2017 De La Rama et al.
2017/0367756 A1 12/2017 Sliwa et al.
2018/0008203 A1 1/2018 Iyun et al.
2018/0028084 A1 2/2018 Williams et al.
2018/0042667 A1 2/2018 Pappone et al.
2018/0049803 A1 2/2018 Solis
2018/0050190 A1 2/2018 Masson
2018/0055563 A1 3/2018 Shetake et al.
2018/0056038 A1 3/2018 Aujla
2018/0070845 A1 3/2018 Hoitink et al.
2018/0071017 A1 3/2018 Bar-Tal et al.
2018/0085064 A1 3/2018 Auerbach et al.
2018/0116539 A1 5/2018 Olson et al.
2018/0132749 A1 5/2018 Govari et al.
2018/0137687 A1 5/2018 Katz et al.
2018/0160978 A1 6/2018 Cohen et al.
2018/0168511 A1 6/2018 Hall et al.
2018/0192958 A1 7/2018 Wu
2018/0206792 A1 7/2018 Auerbach et al.
2018/0235692 A1 8/2018 Efimov et al.
2018/0249959 A1 9/2018 Osypka
2018/0256109 A1 9/2018 Wu et al.
2018/0279954 A1 10/2018 Hayam et al.
2018/0303361 A1 10/2018 Wu et al.
2018/0303414 A1 10/2018 Toth et al.
2018/0310987 A1 11/2018 Altmann et al.
2018/0311497 A1 11/2018 Viswanathan et al.
2018/0338722 A1 11/2018 Altmann et al.
2018/0344202 A1 12/2018 Bar-Tal et al.
2018/0344251 A1 12/2018 Harlev et al.
2018/0344393 A1 12/2018 Gruba et al.
2018/0360534 A1 12/2018 Teplitsky et al.
2018/0365355 A1 12/2018 Auerbach et al.
2019/0000540 A1 1/2019 Cohen et al.
2019/0008582 A1 1/2019 Govari et al.
2019/0015007 A1 1/2019 Rottmann et al.
2019/0030328 A1 1/2019 Stewart et al.
2019/0053708 A1 2/2019 Gliner
2019/0059766 A1 2/2019 Houben et al.
2019/0069950 A1 3/2019 Viswanathan et al.
2019/0069954 A1 3/2019 Cohen et al.
2019/0099585 A1 4/2019 De La Rama et al.
2019/0117111 A1 4/2019 Osadchy et al.
2019/0117303 A1 4/2019 Claude et al.
2019/0117315 A1 4/2019 Keyes et al.
2019/0125439 A1 5/2019 Rohl et al.
2019/0133552 A1 5/2019 Shemesh et al.
2019/0142293 A1 5/2019 Solis
2019/0164633 A1 5/2019 Ingel et al.
2019/0167137 A1 6/2019 Bar-Tal et al.
2019/0167140 A1 6/2019 Williams et al.
2019/0188909 A1 6/2019 Yellin et al.
2019/0192221 A1 6/2019 Pappone et al.
2019/0201664 A1 7/2019 Govari
2019/0209089 A1 7/2019 Baram et al.
2019/0216346 A1 7/2019 Ghodrati et al.
2019/0216347 A1 7/2019 Ghodrati et al.
2019/0231421 A1 8/2019 Viswanathan et al.
2019/0231423 A1 8/2019 Weinkam et al.
2019/0239811 A1 8/2019 Just et al.
2019/0246935 A1 8/2019 Govari et al.
2019/0275291 A2 9/2019 De et al.
2019/0282116 A1 9/2019 Olson
2019/0298442 A1 10/2019 Ogata et al.
2019/0314083 A1 10/2019 Herrera et al.

(56) References Cited

U.S. PATENT DOCUMENTS

2019/0328260 A1 10/2019 Zeidan et al.
2019/0343580 A1 11/2019 Nguyen et al.
2019/0350649 A1 11/2019 Sutermeister et al.
2020/0000518 A1 1/2020 Kiernan et al.
2020/0008705 A1 1/2020 Ziv-Ari et al.
2020/0009378 A1 1/2020 Stewart et al.
2020/0015890 A1 1/2020 To et al.
2020/0022653 A1 1/2020 Moisa
2020/0029845 A1 1/2020 Baram et al.
2020/0038101 A1 2/2020 Tobey et al.
2020/0038103 A1 2/2020 Pappone et al.
2020/0046421 A1 2/2020 Govari
2020/0046423 A1 2/2020 Viswanathan et al.
2020/0060569 A1 2/2020 Tegg
2020/0077959 A1 3/2020 Altmann et al.
2020/0093539 A1 3/2020 Long et al.
2020/0129089 A1 4/2020 Gliner et al.
2020/0129125 A1 4/2020 Govari et al.
2020/0129128 A1 4/2020 Gliner et al.
2020/0138378 A1 5/2020 De La Rama et al.
2020/0163707 A1 5/2020 Sliwa et al.
2020/0179650 A1 6/2020 Beeckler et al.
2020/0196896 A1 6/2020 Solis
2020/0205689 A1 7/2020 Squires et al.
2020/0205690 A1 7/2020 Williams et al.
2020/0205737 A1 7/2020 Beeckler
2020/0205876 A1 7/2020 Govari
2020/0205892 A1 7/2020 Viswanathan et al.
2020/0206456 A1 7/2020 De La Rama et al.
2020/0206498 A1 7/2020 Arora et al.
2020/0289197 A1 9/2020 Viswanathan et al.
2020/0297234 A1 9/2020 Houben et al.
2020/0297281 A1 9/2020 Basu et al.
2020/0297996 A1 9/2020 De La Rama et al.
2020/0305726 A1 10/2020 Salvestro et al.
2020/0305946 A1 10/2020 Desimone et al.
2020/0330752 A1 10/2020 De La Rama et al.
2020/0345262 A1 11/2020 Selkee et al.
2020/0397328 A1 12/2020 Altmann et al.
2020/0398048 A1 12/2020 Krimsky et al.
2021/0015549 A1 1/2021 Haghighi-Mood et al.
2021/0015551 A1 1/2021 Fuentes-Ortega et al.
2021/0022684 A1 1/2021 Govari et al.
2021/0045805 A1 2/2021 Govari et al.
2021/0059549 A1 3/2021 Urman et al.
2021/0059550 A1 3/2021 Urman et al.
2021/0059608 A1 3/2021 Beeckler et al.
2021/0059743 A1 3/2021 Govari
2021/0059747 A1 3/2021 Krans et al.
2021/0077184 A1 3/2021 Basu et al.
2021/0082157 A1 3/2021 Rosenberg et al.
2021/0085200 A1 3/2021 Auerbach et al.
2021/0085204 A1 3/2021 Auerbach et al.
2021/0085215 A1 3/2021 Auerbach et al.
2021/0085387 A1 3/2021 Amit et al.
2021/0093292 A1 4/2021 Baram et al.
2021/0093294 A1 4/2021 Shemesh et al.
2021/0093374 A1 4/2021 Govari et al.
2021/0093377 A1 4/2021 Herrera et al.
2021/0100612 A1 4/2021 Baron et al.
2021/0127999 A1 5/2021 Govari et al.
2021/0128010 A1 5/2021 Govari et al.
2021/0133516 A1 5/2021 Govari et al.
2021/0145282 A1 5/2021 Bar-Tal et al.
2021/0161592 A1 6/2021 Altmann et al.
2021/0169421 A1 6/2021 Govari
2021/0169550 A1 6/2021 Govari et al.
2021/0169567 A1 6/2021 Govari et al.
2021/0169568 A1 6/2021 Govari et al.
2021/0177294 A1 6/2021 Gliner et al.
2021/0177356 A1 6/2021 Gliner et al.
2021/0177503 A1 6/2021 Altmann et al.
2021/0178166 A1 6/2021 Govari et al.
2021/0186363 A1 6/2021 Gliner et al.
2021/0186604 A1 6/2021 Altmann et al.
2021/0187241 A1 6/2021 Govari et al.
2021/0196372 A1 7/2021 Altmann et al.
2021/0196394 A1 7/2021 Govari et al.
2021/0212591 A1 7/2021 Govari et al.
2021/0219904 A1 7/2021 Yarnitsky et al.
2021/0278936 A1 9/2021 Katz et al.
2021/0282659 A1 9/2021 Govari et al.
2021/0307815 A1 10/2021 Govari et al.
2021/0308424 A1 10/2021 Beeckler et al.
2021/0338319 A1 11/2021 Govari et al.
2021/0369132 A1 12/2021 Van Niekerk et al.
2021/0369339 A1 12/2021 Salazar et al.
2022/0054198 A1* 2/2022 Tegg .................... A61B 5/6859
2022/0104873 A1 4/2022 Beeckler et al.

FOREIGN PATENT DOCUMENTS

CN 103220994 A 7/2013
CN 103298392 A 9/2013
CN 102892453 B 4/2015
CN 104968261 A 10/2015
CN 102665586 B 3/2016
CN 103298392 B 8/2016
CN 104968261 B 5/2019
CN 111248993 A 6/2020
CN 111248996 A 6/2020
EP 0668740 A1 8/1995
EP 0644738 B1 3/2000
EP 0727183 B1 11/2002
EP 0727184 B1 12/2002
EP 2166936 A1 3/2010
EP 2173426 A1 4/2010
EP 2166936 A4 7/2010
EP 2173426 A4 7/2010
EP 2429436 A1 3/2012
EP 2470101 A1 7/2012
EP 2544749 A1 1/2013
EP 2568906 A1 3/2013
EP 2470101 A4 6/2013
EP 2613686 A1 7/2013
EP 2613723 A1 7/2013
EP 2544749 A4 10/2013
EP 2568906 A4 5/2014
EP 2613686 A4 7/2014
EP 2783651 A1 10/2014
EP 2613723 A4 4/2015
EP 2544749 B1 8/2015
EP 2907462 A1 8/2015
EP 2908723 A1 8/2015
EP 2699151 B1 11/2015
EP 2699152 B1 11/2015
EP 1585446 B1 12/2015
EP 2699153 B1 12/2015
EP 2977020 A1 1/2016
EP 2173426 B1 4/2016
EP 2498706 B1 4/2016
EP 3023052 A1 5/2016
EP 2429436 B1 11/2016
EP 3111872 A1 1/2017
EP 3146926 A1 3/2017
EP 2578173 B1 6/2017
EP 3184037 A1 6/2017
EP 2568906 B1 8/2017
EP 2613723 B1 10/2017
EP 2977020 B1 11/2017
EP 3238645 A1 11/2017
EP 2884931 B1 1/2018
EP 3300681 A1 4/2018
EP 2613686 B1 9/2018
EP 2349440 B1 8/2019
EP 3527125 A1 8/2019
EP 3300681 B1 11/2019
EP 3318211 B1 12/2019
EP 3581135 A1 12/2019
EP 2736434 B1 2/2020
EP 2908723 B1 3/2020
EP 3451962 B1 3/2020
EP 2470101 B1 5/2020
EP 3679861 A1 7/2020

(56) References Cited

FOREIGN PATENT DOCUMENTS

| | | | |
|---|---|---|---|
| EP | 3733103 | A1 | 11/2020 |
| EP | 3738508 | A1 | 11/2020 |
| EP | 3738509 | A1 | 11/2020 |
| EP | 3972510 | A1 | 3/2022 |
| JP | 2012525933 | A | 10/2012 |
| JP | 2013516218 | A | 5/2013 |
| JP | 2013521892 | A | 6/2013 |
| JP | 2014501557 | A | 1/2014 |
| JP | 2014502195 | A | 1/2014 |
| JP | 5539498 | B2 | 7/2014 |
| JP | 2014158957 | A | 9/2014 |
| JP | 5753862 | B2 | 7/2015 |
| JP | 5778823 | B2 | 9/2015 |
| JP | 2015211874 | A | 11/2015 |
| JP | 2016502912 | A | 2/2016 |
| JP | 6050522 | B2 | 12/2016 |
| JP | 6059535 | B2 | 1/2017 |
| JP | 6078471 | B2 | 2/2017 |
| JP | 2017077479 | A | 4/2017 |
| JP | 2017176879 | A | 10/2017 |
| JP | 6445509 | B2 | 12/2018 |
| JP | 2019030685 | A | 2/2019 |
| WO | 9421167 | A1 | 9/1994 |
| WO | 9421169 | A1 | 9/1994 |
| WO | 9625095 | A1 | 8/1996 |
| WO | 9634560 | A1 | 11/1996 |
| WO | 0182814 | A2 | 11/2001 |
| WO | 2004087249 | A2 | 10/2004 |
| WO | 2008124602 | A1 | 10/2008 |
| WO | 2008124619 | A1 | 10/2008 |
| WO | 2009006616 | A1 | 1/2009 |
| WO | 2009023385 | A1 | 2/2009 |
| WO | 2010129661 | A1 | 11/2010 |
| WO | 2011081686 | A1 | 7/2011 |
| WO | 2011112814 | A1 | 9/2011 |
| WO | 2011159861 | A2 | 12/2011 |
| WO | 2011159955 | A1 | 12/2011 |
| WO | 2011159861 | A3 | 2/2012 |
| WO | 2012068505 | A1 | 5/2012 |
| WO | 2012071087 | A1 | 5/2012 |
| WO | 2012100185 | A2 | 7/2012 |
| WO | 2012068505 | A9 | 10/2012 |
| WO | 2013052852 | A1 | 4/2013 |
| WO | 2013162884 | A1 | 10/2013 |
| WO | 2013173917 | A1 | 11/2013 |
| WO | 2013176881 | A1 | 11/2013 |
| WO | 2014113612 | A1 | 7/2014 |
| WO | 2014176205 | A1 | 10/2014 |
| WO | 2015095577 | A1 | 6/2015 |
| WO | 2015130824 | A1 | 9/2015 |
| WO | 2016001015 | A1 | 1/2016 |
| WO | 2016019760 | A1 | 2/2016 |
| WO | 2016044687 | A1 | 3/2016 |
| WO | 2017192542 | A2 | 11/2017 |
| WO | 2017192712 | A1 | 11/2017 |
| WO | 2018111600 | A1 | 6/2018 |
| WO | 2018191149 | A1 | 10/2018 |
| WO | 2019084442 | A1 | 5/2019 |
| WO | 2019143960 | A1 | 7/2019 |
| WO | 2020026217 | A1 | 2/2020 |
| WO | 2020206328 | A1 | 10/2020 |

OTHER PUBLICATIONS

Extended European Search Report for European Application No. 20199175.9, mailed Mar. 30, 2021, 07 Pages.

Extended European Search Report for European Application No. 20199230.2, mailed Mar. 18, 2021, 05 Pages.

Extended European Search Report for European Application No. 22194801.1, mailed Dec. 23, 2022, 9 pages.

Extended European Search Report for European Application No. 23163381.9 mailed on May 11, 2023, 5 pages.

International Search Report and Written Opinion issued in International Patent Application No. PCT/IB2022/056738, mailed Oct. 21, 2022, 10 pages.

Extended European Search Report and Search Opinion dated Jun. 6, 2024, from corresponding EP Application No. 23219709.5.

* cited by examiner

MULTI-ELECTRODE CATHETER WITH INTERLACED SUBSTRATE

CROSS-REFERENCE TO RELATED APPLICATIONS

This application claims the benefit of prior filed U.S. Provisional Patent Application No. 63/477,673 filed on Dec. 29, 2022, which is hereby incorporated by reference as set forth in full herein.

FIELD

The present invention relates generally to multi-electrode catheters for diagnostic and therapeutic purposes and particularly to planar multi-electrode catheters.

BACKGROUND

Cardiac arrhythmias, such as atrial fibrillation (AF), occur when regions of cardiac tissue abnormally conduct electric signals to adjacent tissue. This disrupts the normal cardiac cycle and causes asynchronous rhythm. Certain procedures exist for treating arrhythmia, including surgically disrupting the origin of the signals causing the arrhythmia and disrupting the conducting pathway for such signals. By selectively ablating cardiac tissue by application of energy via a catheter, it is possible to cease or modify the propagation of unwanted electrical signals from one portion of the heart to another.

Many current ablation approaches in the art tend to utilize radiofrequency (RF) electrical energy to heat tissue. RF ablation can have certain rare drawbacks due to operator's skill, such as heightened risk of thermal cell injury which can lead to tissue charring, burning, steam pop, phrenic nerve palsy, pulmonary vein stenosis, and esophageal fistula. Cryoablation is an alternative approach to RF ablation that can reduce some thermal risks associated with RF ablation but may present tissue damage due to the very low temperature nature of such devices. Maneuvering cryoablation devices and selectively applying cryoablation, however, is generally more challenging compared to RF ablation; therefore, cryoablation is not viable in certain anatomical geometries which may be reached by electrical ablation devices.

Some ablation approaches use irreversible electroporation (IRE) to ablate cardiac tissue using nonthermal ablation methods. IRE delivers short pulses of high voltage to tissues and generates an unrecoverable permeabilization of cell membranes. Delivery of IRE energy to tissues using multi-electrode catheters was previously proposed in the patent literature. Examples of systems and devices configured for IRE ablation are disclosed in U.S. Patent Pub. No. 2021/0169550A1, 2021/0169567A1, 2021/0169568A1, 2021/0161592A1, 2021/0196372A1, 2021/0177503A1, and 2021/0186604A1, each of which are incorporated herein by reference and attached to the Appendix of priority patent Application No. 63/477,673.

The same or different catheter can be used to perform ablation and mapping, which respectively have different design considerations. Alternative catheter designs are therefore desired to meet various design requirements for mapping and/or ablation treatments.

SUMMARY

Catheters are presented herein having at least one electrode pair with a first electrode in the pair configured to contact tissue to receive and/or apply electrical signals for mapping and/or ablation and a second electrode in the pair being positioned facing an opposite direction, away from the tissue, and configured to function as a reference electrode for the first electrode. The first and second electrodes are positioned on separate substrates that are interwoven with each other.

An example end effector of a catheter includes a planar substrate, an interlaced substrate, and an electrode pair. The planar substrate can extend along a longitudinal axis. The planar substrate can include openings therethrough. The interlaced substrate can traverse on a first side of the end effector across a first side of the planar substrate, extend through an opening through the planar substrate, and traverse on a second side of the end effector across a second side of the planar substrate opposite the first side of the planar substrate. The electrode pair can include an electrode affixed to the planar substrate and an electrode affixed to the interlaced substrate substantially opposite the electrode affixed to the planar substrate.

The planar substrate can further include a frame, a first membrane, and a second membrane. The frame can include one or more struts extending along the longitudinal axis. The first membrane can extend between the one or more struts on a first side of the planar substrate facing the first side of the end effector. The second membrane can extend between the one or more struts on a second side of the planar substrate facing the second side of the end effector. A portion of the first membrane can be exposed to ambient environment. A portion of the first membrane can be traversed by the interlaced substrate. A portion of the second membrane can be exposed to ambient environment. A portion of the second membrane can be traversed by the interlaced substrate.

The electrodes of the electrode pair can be exposed to ambient environment.

A first electrode of the electrode pair can be configured to contact tissue. A second electrode of the electrode pair can be configured as a reference electrode to the first electrode.

A center of a first electrode of the electrode pair can be substantially aligned with a center of a second electrode of the electrode pair.

The planar substrate can further include a frame and a membrane. The frame can include a pair of longitudinally extending struts that extend along the longitudinal axis. The membrane can extend over each strut of the pair of longitudinally extending struts and between the pair of longitudinally extending struts. The electrode affixed to the planar substrate of the electrode pair can be affixed to the membrane and between the pair of longitudinally extending struts.

The end effector can include an array of at least four electrodes on the first side of the end effector. The array can include an electrode of the electrode pair that is on the first side of the end effector. The electrodes of the array can be coplanar with each other.

Another example end effector of a catheter can include a plurality of spines, an interlaced substrate, and an electrode pair. The interlaced substrate can traverse across a first spine of the plurality of spines on a first side of the end effector and traverse across a second spine of the plurality of spines on a second side of the end effector. The electrode pair can include an electrode affixed to a spine of the plurality of spines and an electrode affixed the interlaced substrate substantially opposite the electrode affixed to the spine.

The electrodes of the electrode pair can be exposed to ambient environment.

A first electrode of the electrode pair can be configured to contact tissue. A second electrode of the electrode pair can be configured as a reference electrode to the first electrode.

A center of a first electrode of the electrode pair can be substantially aligned with a center of a second electrode of the electrode pair.

The plurality of spines can be substantially coplanar.

The end effector can include a loop member having two spines of the plurality of spines and a connecting member joining distal ends of the two spines.

The end effector can include a first loop member and a second loop member. The first loop member can include a first pair of spines of the plurality of spines and a first connecting member joining distal ends of spines of the first pair of spines. The second loop member can include a second pair of spines of the plurality of spines and a second connecting member joining distal ends of spines of the second pair of spines. The interlaced substrate can traverse each spine of the first pair of spines and the second pair of spines. The end effector can further include a first plurality of electrodes and a second plurality of electrodes. The first plurality of electrodes can include a respective electrode affixed to each spine of the first pair of spines. The second plurality of electrodes can be affixed to the interlaced substrate and respectively opposite at least a portion of the first plurality of electrodes.

Another end effector of a catheter can include a top side, a bottom side, a first substrate portion, a second substrate portion, an opening between the first and second substrate portions, an interlaced substrate, a first electrode pair, and a second electrode pair. The bottom side is opposite the top side. The interlaced substrate can traverse on the top side of the end effector across the first substrate portion, extend through the opening, and traverse on a bottom side of the end effector across the second substrate portion. The first electrode pair can have a bottom electrode affixed to the first substrate portion on the bottom side of the end effector and a top electrode affixed to the interlaced substrate on the top side of the end effector. The top electrode can be disposed substantially opposite the bottom electrode of the first electrode pair. The second electrode pair can include a top electrode affixed to the second substrate portion on the top side of the end effector and a bottom electrode affixed to the interlaced substrate on the bottom side of the end effector. The bottom electrode can be disposed substantially opposite the top electrode of the second electrode pair.

Electrodes of the first electrode pair and the second electrode pair each can be exposed to ambient environment.

The top electrodes of the first electrode pair and the second electrode pair can be configured to contact tissue. The bottom electrodes of the first electrode pair and the second electrode pair can be configured as reference electrodes for the top electrode in the respective electrode pair.

The interlaced substrate can be a first interlaced substrate, and the end effector can further include a second interlaced substrate extending through the opening and traversing on the top side of the end effector and the bottom side of the end effector.

The first substrate portion, the second substrate portion, and the opening can each be elongated along a longitudinal axis. The interlaced substrate can extend orthogonal to the longitudinal axis.

The interlaced substrate can include a flex circuit.

The end effector can include an array of at least four electrodes on the top side of the end effector. The array can include the top electrodes of the first electrode pair and the second electrode pair. The electrodes of the array can be coplanar with each other.

The end effector can further include a support frame configured to move the first substrate portion, the second substrate portion, and the interlaced substrate into a predetermined shape. The predetermined shape being planar. Alternatively, the predetermined shape can be selected from a group including a spheroid, conic or truncated cone.

The support frame can include a plurality of longitudinally extending struts.

The end effector can further include a contiguous substrate including the first substrate portion and the second substrate portion. The contiguous substrate can further include a first membrane and a second membrane. The first membrane can face the top side of the end effector such that a portion of the first membrane is exposed to ambient environment and a portion of the first membrane is traversed by the interlaced substrate. The second membrane can face the bottom side of the end effector such that a portion of the second membrane is exposed to ambient environment and a portion of the second membrane is traversed by the interlaced substrate. The contiguous substrate can further include a nitinol support frame extending through the first substrate portion and/or the second substrate portion. The frame can have longitudinally extending struts, and at least one of the membrane portions can be disposed between the longitudinally extending struts.

The end effector can further include a support frame assembly having a first longitudinally extending strut and a second longitudinally extending strut such that the first substrate portion includes the first longitudinally extending strut and the second substrate portion includes the second longitudinally extending strut. The first longitudinally extending strut can be disposed between electrodes of the first electrode pair. The second longitudinally extending strut can be disposed between a electrodes of the second electrode pair.

The end effector can further include a third substrate portion, a fourth substrate portion, and respective openings between the second and third substrate portions and the third and fourth substrate portions. The interlaced substrate can traverse the third substrate portion and the fourth substrate portion. The interlaced substrate can extend through the respective openings and traverse on the bottom side of the end effector across the third substrate portion and traverse on the top side of the end effector across the fourth substrate portion.

The support frame assembly can further include a third longitudinally extending strut and a fourth longitudinally extending strut such that the third substrate portion includes the third longitudinally extending strut and the fourth substrate portion includes the fourth longitudinally extending strut. The support frame assembly can further include a first connecting strut and a second connecting strut such that the first connecting strut joins the first longitudinally extending strut and the third longitudinally extending strut, and the second connecting strut joins the second longitudinally extending strut and the fourth longitudinally extending strut. The first connecting strut can be arcuate, and the second connecting strut can be arcuate.

BRIEF DESCRIPTION OF THE DRAWINGS

The above and further aspects of this invention are further discussed with reference to the following description in conjunction with the accompanying drawings, in which like numerals indicate like structural elements and features in various figures. The drawings are not necessarily to scale, emphasis instead being placed upon illustrating principles of the invention. The figures depict one or more implementations of the inventive devices, by way of example only, not by way of limitation.

DETAILED DESCRIPTION

The following detailed description should be read with reference to the drawings, which depict selected embodiments and are not intended to limit the scope of the invention. This description enables one skilled in the art to make and use the invention, and describes several embodiments, adaptations, variations, alternatives and uses of the invention, including what is presently believed to be the best mode of carrying out the invention. Any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those skilled in the pertinent art in view of the teachings herein. Such modifications and variations are intended to be included within the scope of the claims.

As used herein, the terms "patient," "host." "user," and "subject" refer to any human or animal subject and are not intended to limit the systems or methods to human use, although use of the subject invention in a human patient represents a preferred embodiment. As well, the term "proximal" indicates a location closer to the operator whereas "distal" indicates a location further away to the operator or physician.

Figure 1:
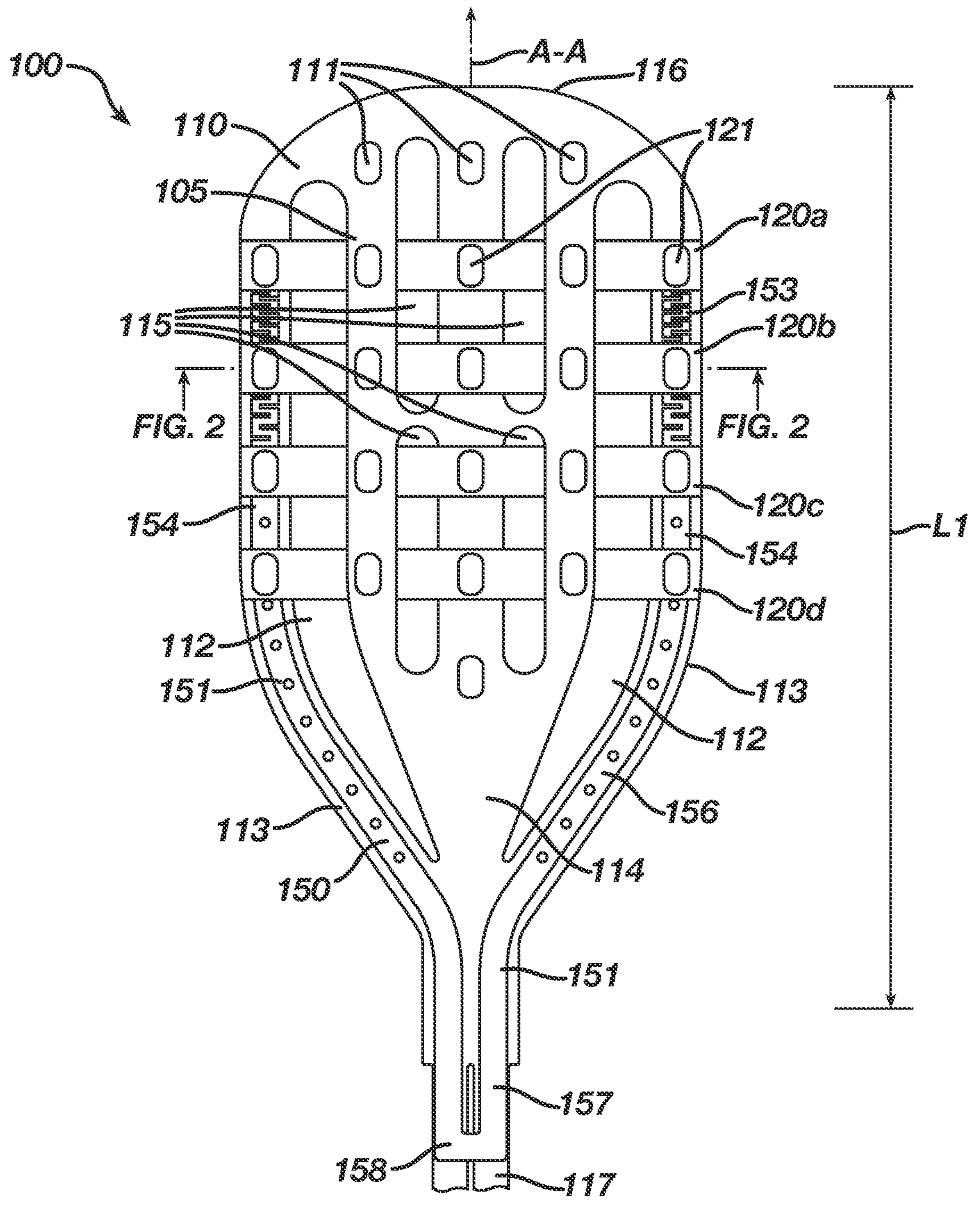
FIG. 1 is an illustration of a first example end effector of a catheter according to aspects of the present invention.

FIG. 1 is an illustration of a first example end effector 100 of a catheter. The end effector 100 includes a planar substrate 110 and multiple interlaced substrates 120*a*. 120*b*, 120*c*, 120*d* that go over and under portions of the planar substrate 110 at overlapping regions 105. The end effector 100 includes electrodes 111 affixed to the planar substrate and electrodes 121 affixed to the interlaced substrates 120*a*, 120*b*, 120*c*, 120*d*. A first side 101 (FIG. 2) of the end effector 100 is illustrated in FIG. 1. The first side 101 includes an array of electrodes 111, 121 that are coplanar with each other. The end effector 100 can have a second side 102 (FIG. 2) opposite the first side with one or more electrodes such that at least one electrode on the second side is opposite an electrode on the first side, forming an electrode pair with the opposite electrode.

Figure 6:
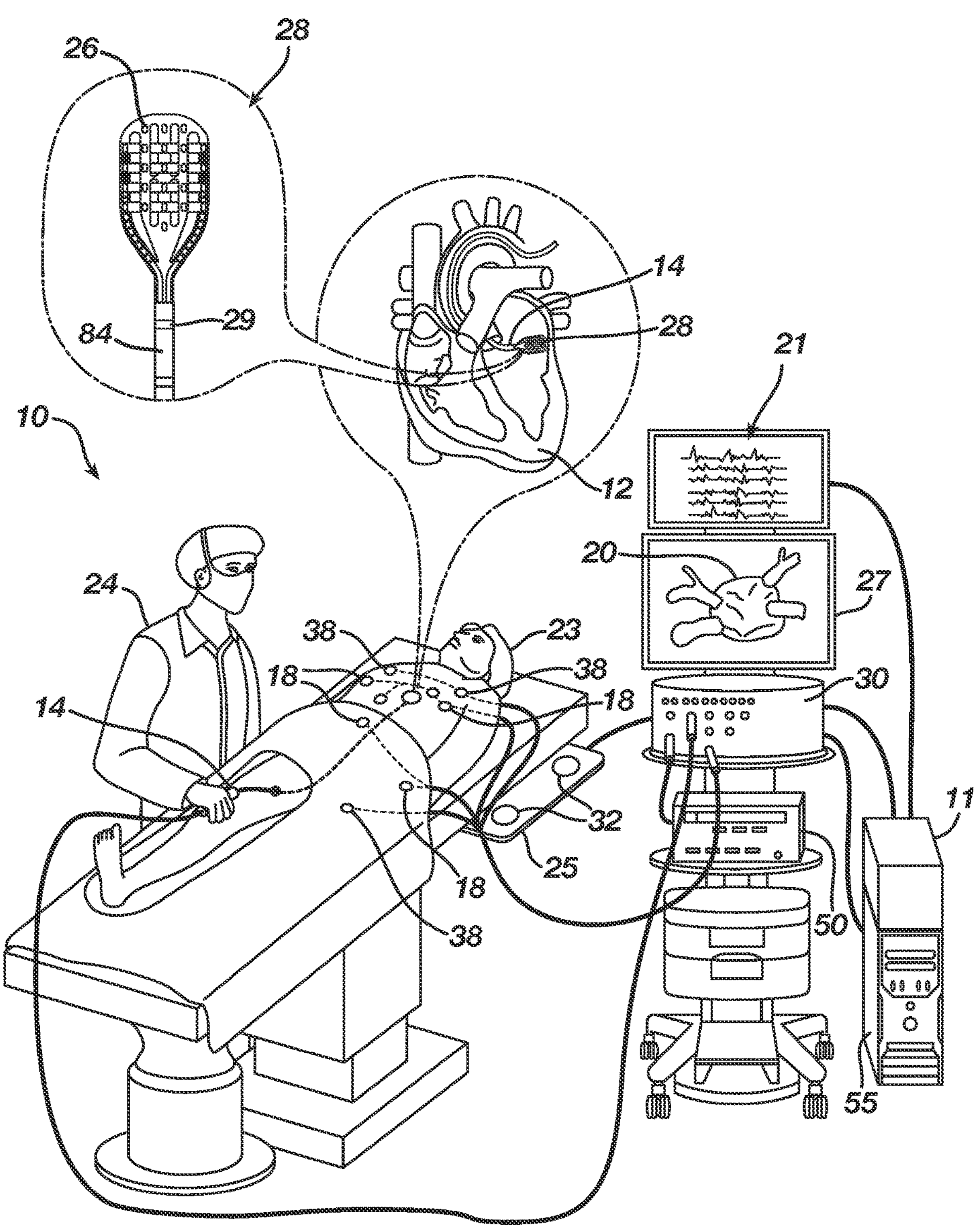
FIG. 6 is an illustration of an example catheter-based electrophysiology mapping and ablation system according to aspects of the present invention.

The planar substrate 110 extends along a longitudinal axis A-A and includes openings 112, 115 through the planar substrate 110. The interlaced substrates 120*a*, 120*b*, 120*c*, 120*d* extend through the openings 112, 115 to interlace with the planar substrate 110. The openings include two outer longitudinal openings 112 that extend along the longitudinal axis A-A and through a majority of a length L1 of the end effector 100. The two outer longitudinal openings 112 divide the planar substrate 110 into outer portions 113 and a central portion 114. The openings include central longitudinal openings 115 that are between the outer longitudinal openings 112 and extend along the longitudinal axis A-A within the central portion 114 of the planar substrate 110. The planar substrate 110 includes a distal arc 116 at a distal end of the end effector 100. The planar substrate 110 includes a proximal extension 117 that is configured to be coupled to a catheter shaft to form a catheter 14 (FIG. 6).

The planar substrate 110 further includes a support frame 150 having a proximal connecting portion 158 joining two distally extending struts 151. The struts 151 include proximal strut portions 157 extending distally from the proximal connecting portion 158 and along the longitudinal axis A-A, angled strut portions 156 extending distally from the proximal strut portions 157 and angling away from the longitudinal axis A-A, and outer strut portions 154 extending parallel to each other along the longitudinal axis A-A distal of the angled strut portions 156 and including a graduated cut pattern 153. At least some of the electrodes 121 positioned in the outer portions 113 of the planar substrate 110 are positioned over the outer strut portions 154. A majority of electrodes 121, 111 are positioned between the outer strut portions 154.

The interlaced substrates 120*a*, 120*b*, 120*c*, 120*d* are manufactured as separate from the planar substrate 110 and are coupled to the planar substrate 110 with a coupling mechanism, which can include adhesive, weld, rivet, or other suitable coupling means as understood by a person skilled in the pertinent art. The interlaced substrates 120*a*, 120*b*, 120*c*, 120*d* are affixed to the outer portions 113 of the planar substrate 110 near ends of the interlaced substrates 120*a*, 120*b*, 120*c*, 120*d*. The interlaced substrates 120*a*, 120*b*, 120*c*, 120*d* may also be coupled to the central portions 114 of the planar substrate 110.

The interlaced substrates 120*a*, 120*b*, 120*c*, 120*d* are perpendicular to the longitudinal axis A-A. The interlaced substrates are woven over and under portions of the planar substrate 110 in an alternating pattern with a fixed distance between interlaced substrates. Alternatively, the interlaced substrates 120*a*, 120*b*, 120*c*, 120*d* need not be interlaced and can each be entirely on one side of the end effector 200. As another alternative, the interlaced substrates 120*a*, 120*b*, 120*c*, 120*d* need not alternate between the sides of the end effector through every available opening 112, 115, but may cross on the same side of the end effector 100 on two or more adjacent portions of the planar substrate 110, then cross through an opening 112, 115 to the opposite side of the end effector 100 to traverse another portion of the planar substrate 110.

Figure 2:
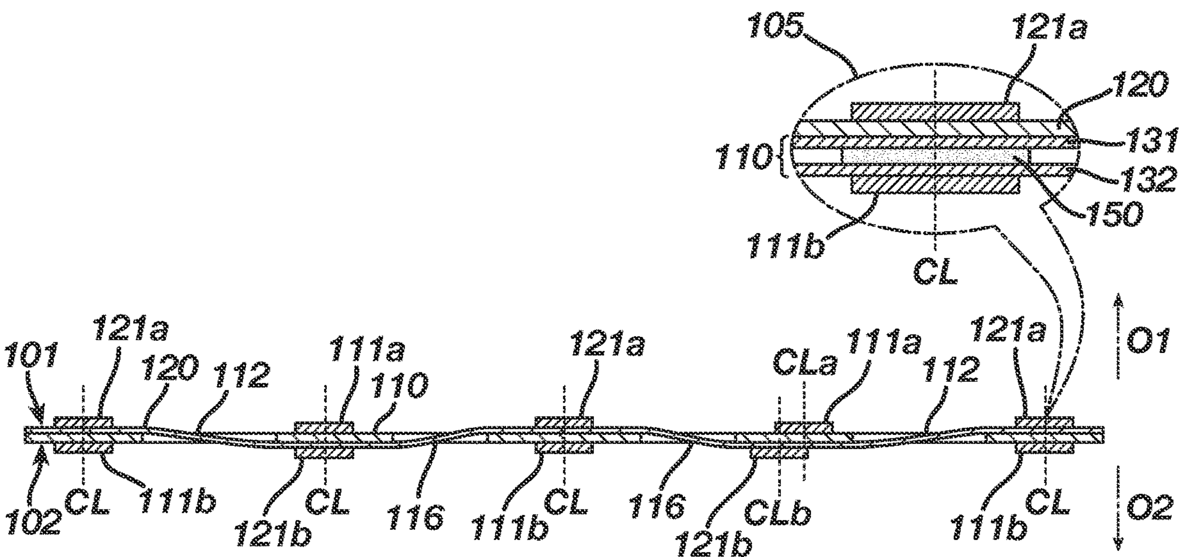
FIG. 2 is a cross-sectional illustration of the first example end effector as indicated in FIG. 1.

FIG. 2 is a cross-sectional illustration of the first example end effector 100 as indicated in FIG. 1. The end effector 100 has a first side 101 facing up and a second side 102 facing down as illustrated in FIG. 2. From left to right, the interlaced substrate 120 is positioned on the first side 101 of the end effector 100 across a first side of the planar substrate 110, extends through an outer longitudinal opening 112 of the planar substrate 110, traverses on the second side 102 of the end effector 100 across a second side of the planar substrate opposite the first side of the planar substrate, extends through a central opening 116 of the planar substrate 110, traverses on the first side 101 of the end effector 100 across the first side of the planar substrate 110, extends through another central opening 116 of the planar substrate 110, traverses on the second side 102 of the end effector 100 across the second side of the planar substrate 110, extends through another outer longitudinal opening 112 of the planar substrate 110, and traverses on the first side 101 of the end effector 100 across the first side of the planar substrate 110.

The end effector 100 includes electrode pairs each having an electrode affixed to the planar substrate 110 and an electrode affixed to the interlaced substrate 120 substantially opposite the electrode affixed to the planar substrate 110. Three of the electrode pairs (right, left and center) include an electrode 121*a* affixed to the interlaced substrate 120 on the first side 101 of the end effector 100 and an electrode 111*b* affixed to the planar substrate 110 on the second side 102 of the end effector 100. Two of the electrode pairs (between the aforementioned three electrode pairs) include an electrode 111*a* affixed to the planar substrate 110 on the first side 101 of the end effector 100 and an electrode 111*b* affixed to the interlaced substrate 120 on the second side 102 of the end effector 100. The electrodes of the electrode pairs are substantially aligned with respect to a center line CL. The centerlines CLa, CLb of the electrodes 111*a*, 121*b* of the fourth electrode pair from the left are not precisely aligned, and electrodes 111*a*, 121*b* in the fourth electrode pair are substantially opposite each other by virtue of having significant overlap within respect to the plane of the planar substrate 110.

Electrodes 111, 121, 131 in the electrode pairs are exposed to ambient environment so that when inserted in a bodily lumen during a treatment, some of the electrodes can be in contact with tissue while other electrodes are in contact with bodily fluid. By being positioned opposite each other, when one electrode in the pair is in contact with tissue, the other electrode can be configured as a reference electrode for the electrode in contact with tissue. The reference electrode can measure an electrical potential of the bodily fluid, which can be compared to an electrical potential of the opposite electrode in the pair that is in contact with tissue.

The electrodes 111, 121, 131 can be configured to function with a system similar to the system 10 illustrated in FIG. 6. The electrodes can be configured for tracking and position orientation of the end effector 100, sensing Intracardiac Electrogram (IEGM) signals, ablating using radiofrequency energy, ablating using irreversible electroporation, or any combination thereof.

The planar substrate 110 further includes a first membrane 131 on the first side of the planar substrate 110 and a second membrane 132 on the second side of the planar substrate 110. The membranes 131, 132 extends between the struts 151 of the frame 150. The first and fifth electrode pairs are over the support frame 150, and the second, third, and fourth electrode pairs are between the struts 151 of the support frame 150. Portions of the membranes 131, 132 are exposed to ambient environment, and portions of the membranes 131, 132 are traversed by the interlacing substrate 120. The membranes 131, 132 can each respectively include a flex circuit that can be configured with conductors, sensors, and/or other compatible features as understood by a person skilled in the art.

For instance, the planar substrate 110 can include features of example end effectors illustrated in FIGS. 1A-G, 2A-E, 3, and 4A-C of U.S. Provisional Patent Application No. 63/403,589 filed Sep. 2, 2022, incorporated herein by reference, a copy of which is attached to the Appendix of priority patent Application No. 63/477,673. The planar substrate 110 can include features of example end effectors illustrated in U.S. patent application Ser. No. 18/230,934 filed Aug. 7, 2023, which is incorporated by reference herein, published as US2024/0065755A1 on Feb. 29, 2024, and claims priority to U.S. 63/403,589. As non-limiting examples, the planar substrate 110 can include electrically conductive traces to make contact to the electrodes 111 and sensors, piezoelectric transducers, planar spiral single axis position sensors, impedance navigation sensor, etc.

Figure 3:
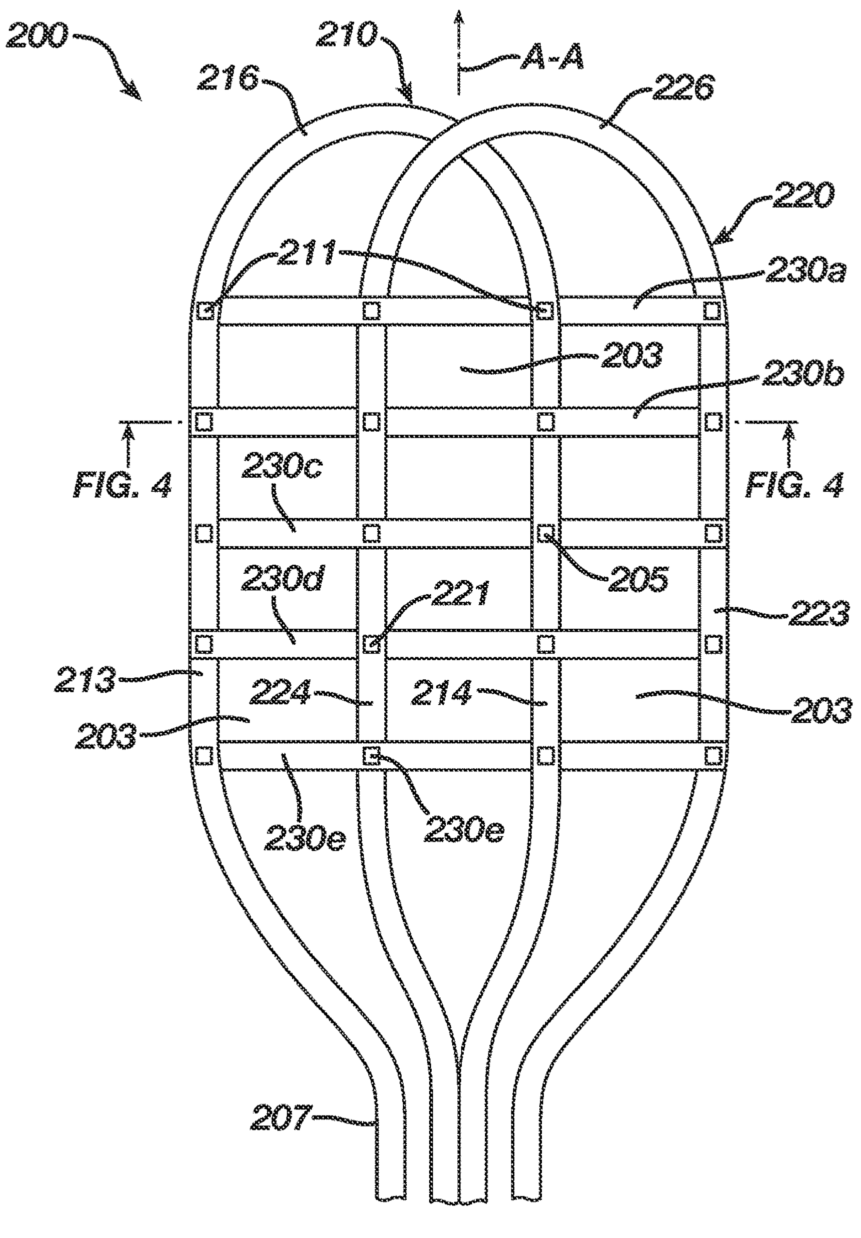
FIG. 3 is an illustration of a second example end effector of a catheter according to aspects of the present invention.

FIG. 3 is an illustration of a second example end effector 200 of a catheter including a first loop 210, a second loop 220, interlaced substrates 230*a*, 230*b*, 230*c*, 230*d*, 230*c*, and electrodes 211, 221, 231. The interlaced substrates 230*a*, 230*b*, 230*c*, 230*d*, 230*e* weave over and under spines 213, 214, 223, 224 of the loops 210, 220. The first loop 210 has a first spine 213 that is on an outer edge of the end effector 200 and a second spine 214 that is positioned centrally within the end effector 200. The second loop 220 has a first spine 223 that is on an outer edge of the end effector 200 and a second spine 224 that is positioned centrally within the end effector 200. The spines 213, 214, 223, 224 are substantially coplanar and aligned along a longitudinal axis A-A. The second spine 214, 224 of each of the first loop 210 and the second loop is positioned between spines of the other loop. The loop members 210, 220 each respectively include a connecting member 216, 226 in the shape of an arc at a distal end of the end effector 200 joining distal ends of the spines 213, 214, 223, 224 of the respective loop members. A first loop member 210 includes a first pair of spines 213, 214 and a first connecting member 216 joining distal ends of the spines 213, 214 of the first pair of spines. A second loop member 220 includes a second pair of spines 223, 224 and a second connecting member 226 joining distal ends of spines 223, 224 of the second pair of spines. A proximal portion 207 of the end effector includes ends of the loop members 210 that are configured to attach to a catheter shaft.

The end effector 200 can include an alternative number of loop members, and preferably includes two or three loop members. The loop members 210, 220 and catheter shaft can include compatible features of catheters having an end effector with loop members as understood by a person skilled in the pertinent art including catheters disclosed in U.S. Patent Publication Nos. 2021/0369339A1 and 2021/0369132A1 incorporated herein by reference, a copy of each of which is attached to the Appendix of priority patent Application No. 63/477,673. For instance, the loop members 210, 220 can include a support frame including nitinol or other suitable material to provide structural support for the loop members, electrical conductors (e.g. wiring, flex circuit traces, etc.) to connect to electrodes 211, 221, irrigation conduits, and the like. The end effector 200 can include an alternative number of loop members, for instance three loop members. The loop members 210, 220 can have an alternative shape as understood by a person skilled in the pertinent art. Alternatively, the end effector 200 can lack one or both connecting members 216, 226 so that the spines 213, 214, 223, 224 have free distal ends such as disclosed in U.S. Pat. No. 9,820,664 incorporated herein by reference, a copy of which is attached to the Appendix of priority patent Application No. 63/477,673.

The interlaced substrates 230*a*, 230*b*, 230*c*, 230*d*, 230*e* are perpendicular to the spines 213, 214, 223, 224 and the longitudinal axis A-A. The interlaced substrates 230*a*, 230*b*, 230*c*, 230*d*, 230*e* traverse each spine of the first pair of spines 213, 214 and the second pair of spines 223, 224. The spines and interlaced substrates are woven over and under each other in an alternating pattern with a fixed distance between spines and interlaced substrates similar to a tennis racket. The spines 213, 214, 223, 224 are positioned with an opening 203 between adjacent spines so that the interlaced substrates 230*a*, 230*b*, 230*c*, 230*d*, 230*e* can traverse across a spine one side of the end effector 200, through the opening 203, and across an adjacent spine on the opposite side of the end effector 200. Alternatively, the substrates 230*a*, 230*b*, 230*c*, 230*d*, 230*e* need not be interlaced and can each be entirely on one side of the end effector 200. As another alternative, the interlaced substrates 230*a*, 230*b*, 230*c*, 230*d*, 230*e* need not alternate between the sides of the end effector between every spine, but may cross on the same side of the end effector on two or more adjacent spines, then cross to the opposite of the end effector to traverse another spine.

The interlaced substrates 230*a*, 230*b*, 230*c*, 230*d*, 230*e* are manufactured separately from the loop members 210, 220 and are coupled to the loop members 210, 220 with a coupling mechanism, which may include adhesive, weld, rivet, or other suitable coupling means as understood by a person skilled in the pertinent art. Ends of the interlaced substrates 230*a*, 230*b*, 230*c*, 230*d*, 230*e* are affixed to the first spines 213, 223. Preferably, the interlaced substrates 230*a*, 230*b*, 230*c*, 230*d*, 230*e* are also affixed to the second spines 214, 224; however, they need not be.

Figure 4:
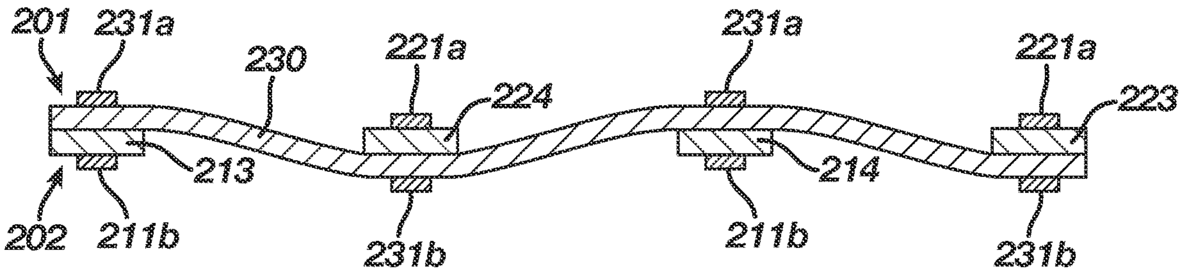
FIG. 4 is a cross-sectional illustration of the second example end effector as indicated in FIG. 3.

FIG. 4 is a cross-sectional illustration of the second example end effector as indicated in FIG. 3. The interlaced substrate 230 is shown traversing across the spines 213, 224, 214, 223 on one side of the end effector, then the other in an alternating fashion. The spines 213, 224, 214, 223 and the interlaced substrate 230 include additional features not illustrated in cross section, such as conductors to electrodes and other structures of loop members 210, 220 as disclosed above. These features are omitted in FIG. 4 purely for the sake of simplicity in the illustration.

At least one, potentially all of the electrodes 211, 221, 231 of the end effector 200 form a respective electrode pair that includes an electrode 211, 221 affixed to a spine 213, 214, 223, 224 and an electrode 231 affixed to an interlaced substrate 230*a*, 230*b*, 230*c*, 230*d*, 230*e*. As illustrated in FIG. 4, a first electrode pair includes an electrode 231*a* on a first side 201 of the end effector 200 that is affixed to the interlaced substrate 230 and an opposite electrode 211*b* on a second side 202 of the end effector 200 that is affixed to the first spine 213 of the first loop member 210. A second electrode pair includes an electrode 221*a* on the first side 201 of the end effector 200 that is affixed to the second spine 224 of the second loop member 220 and an opposite electrode 231*b* on the second side 202 of the end effector 200 that is affixed to the interlaced substrate 230. A third electrode pair includes an electrode 231*a* on the first side 201 of the end effector 200 that is affixed to the interlaced substrate 230 and an opposite electrode 211*b* on the second side 202 of the end effector 200 that is affixed to the second spine 214 of the first loop member 210. Some electrodes 221*a* on the first side 201 of the end effector 200 are therefore affixed to spines 223, 224 of the second loop member 200, and some electrodes 231*a* on the first side 201 of the end effector 200 are therefore affixed to the interlaced substrate 230. Some electrodes 211*b* on the second side 202 of the end effector 200 are affixed to spines 213, 214 of the first loop member 210 and some electrodes 231*b* on the second side 202 of the end effector 200 are affixed to the interlaced substrate 230. Similar to as illustrated in FIG. 2, the opposite electrodes can overlap with respect to a plane of the end effector 200. The opposite electrodes can be aligned with respect to a centerline CL, or the centerlines CLa, CLb of the opposite electrodes can be offset. Electrodes in an electrode pair can be substantially opposite each other by virtue of having significant overlap within respect to a plane of the end effector 200.

Electrodes 211, 221, 231 in the electrode pairs are exposed to ambient environment so that when inserted in a bodily lumen during a treatment, a portion of the electrodes can be in contact with tissue while another portion is in contact with bodily fluid. By being positioned opposite each other, when one electrode in the pair is in contact with tissue, the other electrode can be configured as a reference electrode for the electrode in contact with tissue. The reference electrode can measure an electrical potential of the bodily fluid, which can be compared to an electrical potential of the opposite electrode in the pair that is in contact with tissue.

The electrodes 211, 221, 231 can be configured to function with a system similar to the system 10 illustrated in FIG. 6. The electrodes can be configured for tracking and position orientation of the end effector 100, sensing Intracardiac Electrogram (IEGM) signals, ablating using radiofrequency energy, ablating using irreversible electroporation, or any combination thereof.

Figure 5:
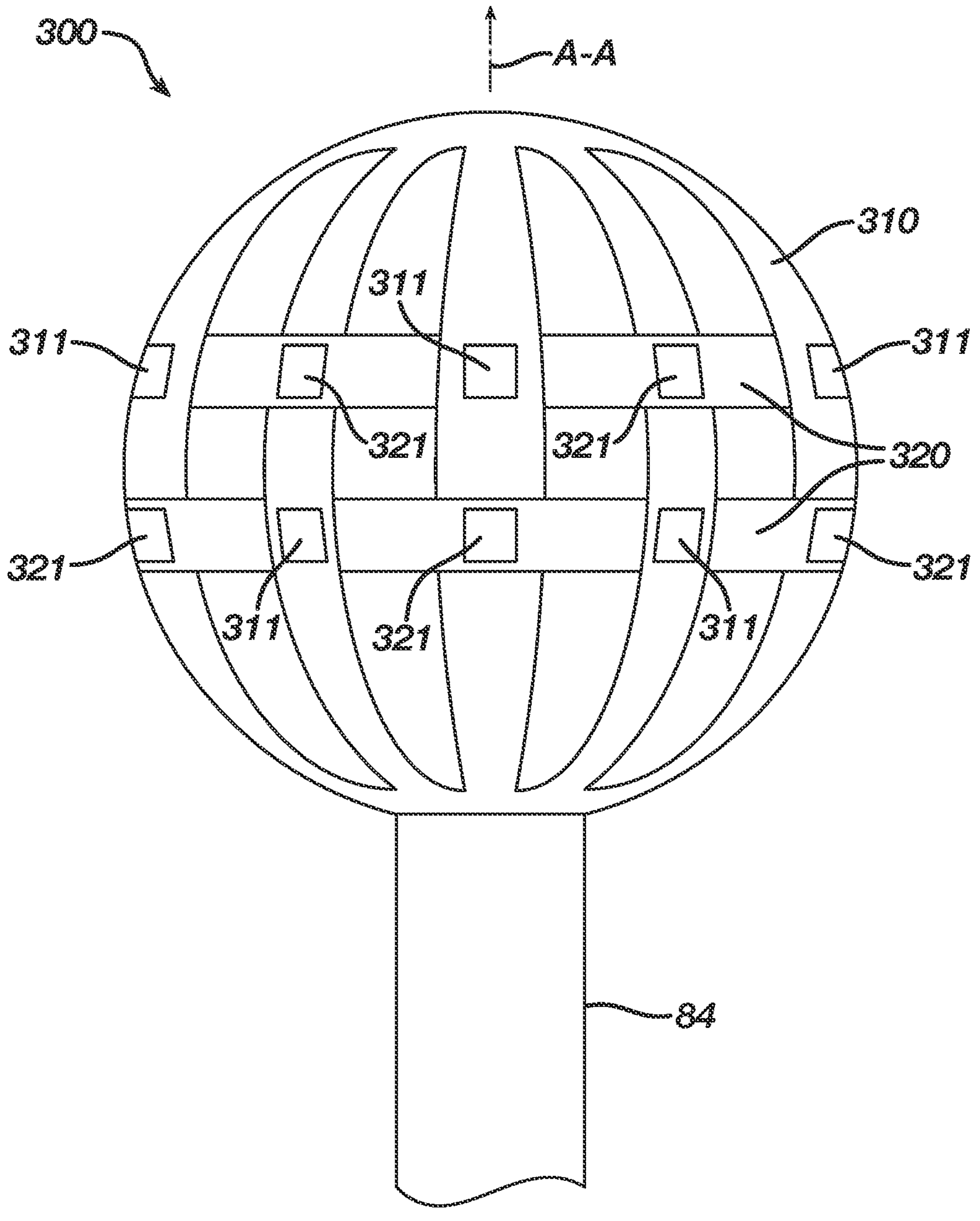
FIG. 5 is an illustration of a third example end effector of a catheter according to aspects of the present invention.

FIG. 5 is an illustration of a third example end effector 300 of a catheter coupled to a shaft 84. The end effector 300 includes a spherical substrate 310 and multiple interlaced substrates 320 that go over and under portions of the spherical substrate 320. The end effector 300 includes electrodes 311 affixed to the spherical substrate 310 and electrodes 321 affixed to the interlaced substrates 320. The illustrated electrodes 311, 321 are on an outer surface of the end effector 300 and therefore are positioned to contact tissue. The end effector 300 can further include one or more electrodes on an inner surface of the end effector 300 that are configured as act as a reference electrode to one or more of the electrodes 311, 321 on the outer surface. At least one electrode on the inner surface can be opposite an electrode on the outer surface, forming an electrode pair with the opposite electrode. The electrode pair can be configured similarly to the electrode pairs disclosed in relation to FIGS. 1 through 4.

The spherical substrate 310 extends along a longitudinal axis A-A and includes openings through the spherical substrate 310. The interlaced substrates 320 extend through the openings to interlace with the spherical substrate 310. The openings can extend longitudinally while the interlaced substrates 320 extend orthogonal to the longitudinal axis A-A. The spherical substrate 310 can further include a support frame.

The third example end effector 300 can include a flex circuit and other features similar to the first example end effector 100, reconfigured in a spherical shape. Likewise, features of the first example end effector 100 can be reconfigured into a cylindrical shape as understood by a person skilled in the pertinent art. Further, the second example end effector 200 can be adapted into a spherical or cylindrical shape as understood by a person skilled in the pertinent art.

FIG. 6 is an illustration showing an example catheter-based electrophysiology mapping and ablation system 10. The system 10 includes multiple catheters, which are percutaneously inserted by a physician 24 through the patient's vascular system into a chamber or vascular structure of a heart 12. Typically, a delivery sheath catheter is inserted into the left or right atrium near a desired location in the heart 12. Thereafter, a plurality of catheters can be inserted into the delivery sheath catheter so as to arrive at the desired location. The plurality of catheters may include catheters dedicated for sensing Intracardiac Electrogram (IEGM) signals, catheters dedicated for ablating and/or catheters dedicated for both sensing and ablating. An example catheter 14 that is configured for sensing IEGM and/or ablation is illustrated herein. The physician 24 brings a distal tip 28 of the catheter 14 into contact with the heart wall for sensing a target site in the heart 12. The distal tip 28 of the catheter can include an end effector configured similarly to the example end effectors 100, 200, 300 disclosed herein, variations thereof, and alternatives thereto as understood by a person skilled in the art. The illustrated catheter 14 include electrodes 26 that can be configured similarly to electrodes 111, 121, 211, 221, 311, 321 of the example end effectors 100, 200, 300 illustrated in FIGS. 1 through 5.

The catheter 14 may additionally include a position sensor 29 embedded in or near distal tip 28 (e.g. in shaft 84) for tracking position and orientation of distal tip 28. Optionally and preferably, position sensor 29 is a magnetic based position sensor including three magnetic coils for sensing three-dimensional (3D) position and orientation.

A magnetic based position sensor 29 may be operated together with a location pad 25 including a plurality of magnetic coils 32 configured to generate magnetic fields in a predefined working volume. Real time position of a distal tip 28 of the catheter 14 may be tracked based on magnetic fields generated with a location pad 25 and sensed by a magnetic based position sensor 29. Details of the magnetic based position sensing technology are described in U.S. Pat. Nos. 5,391,199; 5,443,489; 5,558,091; 6,172,499; 6,239,724; 6,332,089; 6,484,118; 6,618,612; 6,690,963; 6,788,967; 6,892,091 incorporated by reference herein.

The system 10 includes one or more electrode patches 38 positioned for skin contact on the patient 23 to establish location reference for location pad 25 as well as impedance-based tracking of electrodes 26. For impedance-based tracking, electrical current is directed toward electrodes 26 and sensed at electrode skin patches 38 so that the location of each electrode can be triangulated via the electrode patches 38. Details of the impedance-based location tracking technology are described in U.S. Pat. Nos. 7,536,218; 7,756,576; 7,848,787; 7,869,865; and 8,456,182 incorporated by reference herein.

A recorder 11 displays electrograms 21 captured with body surface ECG electrodes 18 and intracardiac electrograms (IEGM) captured with electrodes 26 of the catheter 14. The recorder 11 may include pacing capability for pacing the heart rhythm and/or may be electrically connected to a standalone pacer.

The system 10 can include an ablation energy generator 50 that is adapted to conduct ablative energy to one or more of electrodes at a distal tip of a catheter configured for ablating. Energy produced by the ablation energy generator 50 may include, but is not limited to, radiofrequency (RF) energy or pulsed-field ablation (PFA) energy, including monopolar or bipolar high-voltage DC pulses as may be used to effect irreversible electroporation (IRE), or combinations thereof.

A patient interface unit (PIU) 30 is an interface configured to establish electrical communication between catheters, electrophysiological equipment, power supply and a workstation 55 for controlling operation of system 10. Electrophysiological equipment of the system 10 may include for example, multiple catheters, a location pad 25, body surface ECG electrodes 18, electrode patches 38, an ablation energy generator 50, and a recorder 11. Optionally and preferably, the PIU 30 includes processing capability for implementing real-time computations of location of the catheters and for performing ECG calculations.

The workstation 55 includes memory, processor unit with memory or storage with appropriate operating software loaded therein, and user interface capability. The workstation 55 can be configured to provide multiple functions, optionally including (1) modeling the endocardial anatomy in three-dimensions (3D) and rendering the model or an anatomical map 20 for display on a display device 27; (2) displaying on the display device 27 activation sequences (or other data) compiled from recorded electrograms 21 in representative visual indicia or imagery superimposed on the rendered anatomical map 20; (3) displaying real-time location and orientation of multiple catheters within the heart chamber; and (4) displaying on the display device 27 sites of interest such as places where ablation energy has been applied. One commercial product embodying elements of the system 10 is available as the CARTO™ 3 System, available from Biosense Webster, Inc., 31 Technology Drive, Irvine, CA 92618.

Having shown and described exemplary embodiments of the subject matter contained herein, further adaptations of the methods and systems described herein may be accomplished by appropriate modifications without departing from the scope of the claims. In addition, where methods and steps described above indicate certain events occurring in certain order, it is intended that certain steps do not have to be performed in the order described but in any order as long as the steps allow the embodiments to function for their intended purposes. Therefore, to the extent there are variations of the invention, which are within the spirit of the disclosure or equivalent to the inventions found in the claims, it is the intent that this patent will cover those variations as well. Some such modifications should be apparent to those skilled in the art. For instance, the examples, embodiments, geometrics, materials, dimensions, ratios, steps, and the like discussed above are illustrative. Accordingly, the claims should not be limited to the specific details of structure and operation set forth in the written description and drawings.

The following clauses list non-limiting embodiments of the disclosure:

Clause 1. An end effector of a catheter, the end effector comprising: a planar substrate extending along a longitudinal axis, the planar substrate comprising openings therethrough; and an interlaced substrate traversing on a first side of the end effector across a first side of the planar substrate, extending through an opening through the planar substrate, and traversing on a second side of the end effector across a second side of the planar substrate opposite the first side of the planar substrate; and an electrode pair comprising an electrode affixed to the planar substrate and an electrode affixed to the interlaced substrate substantially opposite the electrode affixed to the planar substrate.

Clause 2. The end effector of clause 1, the planar substrate further comprising: a frame comprising one or more struts extending along the longitudinal axis; a first membrane extending between the one or more struts on a first side of the planar substrate facing the first side of the end effector; and a second membrane extending between the one or more struts on a second side of the planar substrate facing the second side of the end effector.

Clause 3. The end effector of clause 2, a portion of the first membrane being exposed to ambient environment, a portion of the first membrane being traversed by the interlaced substrate, a portion of the second membrane being exposed to ambient environment, and a portion of the second membrane being traversed by the interlaced substrate.

Clause 4. The end effector of any one of clauses 1-3, the electrodes of the electrode pair being exposed to ambient environment.

Clause 5. The end effector of any one of clauses 1-4, a first electrode of the electrode pair being configured to contact tissue, and a second electrode of the electrode pair being configured as a reference electrode to the first electrode.

Clause 6. The end effector of any one of clauses 1-5, in which a center of a first electrode of the electrode pair being substantially aligned with a center of a second electrode of the electrode pair.

Clause 7. The end effector of any one of clauses 1-6, the planar substrate further comprising: a frame comprising a pair of longitudinally extending struts that extend along the longitudinal axis; and a membrane extending over each strut of the pair of longitudinally extending struts, and between the pair of longitudinally extending struts.

Clause 8. The end effector of clause 7, the electrode affixed to the planar substrate of the electrode pair being affixed to the membrane and between the pair of longitudinally extending struts.

Clause 9. The end effector of any one of clauses 1-8, the end effector comprising an array of at least four electrodes on the first side of the end effector, the array comprising an electrode of the electrode pair that is on the first side of the end effector, and the electrodes of the array being coplanar with each other.

Clause 10. An end effector of a catheter, the end effector comprising: a plurality of spines; an interlaced substrate traversing across a first spine of the plurality of spines on a first side of the end effector and traversing across a second spine of the plurality of spines on a second side of the end effector; and an electrode pair comprising an electrode affixed to a spine of the plurality of spines and an electrode affixed the interlaced substrate substantially opposite the electrode affixed to the spine.

Clause 11. The end effector of clause 10, the electrodes of the electrode pair being exposed to ambient environment.

Clause 12. The end effector of clause 10 or 11, a first electrode of the electrode pair being configured to contact tissue, and a second electrode of the electrode pair being configured as a reference electrode to the first electrode.

Clause 13. The end effector of any one of clauses 10-12, in which a center of a first electrode of the electrode pair being substantially aligned with a center of a second electrode of the electrode pair.

Clause 14. The end effector of any one of clauses 10-13, the plurality of spines being substantially coplanar.

Clause 15. The end effector of any one of clauses 10-14, the end effector comprising: a loop member comprising two spines of the plurality of spines and a connecting member joining distal ends of the two spines.

Clause 16. The end effector of any one of clauses 10-15, the end effector comprising: a first loop member comprising a first pair of spines of the plurality of spines and a first connecting member joining distal ends of spines of the first pair of spines; and a second loop member comprising a second pair of spines of the plurality of spines and a second connecting member joining distal ends of spines of the second pair of spines.

Clause 17. The end effector of clause 16, the interlaced substrate traversing each spine of the first pair of spines and the second pair of spines.

Clause 18. The end effector of clause 16 or 17, further comprising: a first plurality of electrodes comprising a respective electrode affixed to each spine of the first pair of spines; and a second plurality of electrodes affixed to the interlaced substrate and respectively opposite at least a portion of the first plurality of electrodes.

Clause 19. An end effector of a catheter, the end effector comprising: a top side; a bottom side opposite the top side; a first substrate portion; a second substrate portion; an opening between the first and second substrate portions; an interlaced substrate traversing on the top side of the end effector across the first substrate portion, extending through the opening, and traversing on a bottom side of the end effector across the second substrate portion; a first electrode pair comprising a bottom electrode affixed to the first substrate portion on the bottom side of the end effector and a top electrode affixed to the interlaced substrate on the top side of the end effector, the top electrode being disposed substantially opposite the bottom electrode of the first electrode pair; and a second electrode pair comprising a top electrode affixed to the second substrate portion on the top side of the end effector and a bottom electrode affixed to the interlaced substrate on the bottom side of the end effector, the bottom electrode being disposed substantially opposite the top electrode of the second electrode pair.

Clause 20. The end effector of clause 19, electrodes of the first electrode pair and the second electrode pair each being exposed to ambient environment.

Clause 21. The end effector of clause 19 or 20, the top electrodes of the first electrode pair and the second electrode pair being configured to contact tissue, and the bottom electrodes of the first electrode pair and the second electrode pair being configured as reference electrodes for the top electrode in the respective electrode pair.

Clause 22. The end effector of any one of clauses 19-21, the interlaced substrate being a first interlaced substrate, and the end effector further comprising: a second interlaced substrate extending through the opening and traversing on the top side of the end effector and the bottom side of the end effector.

Clause 23. The end effector of any one of clauses 19-22, the first substrate portion, the second substrate portion, and the opening each being elongated along a longitudinal axis, and the interlaced substrate extending orthogonal to a longitudinal axis.

Clause 24. The end effector of any one of clauses 19-23, the interlaced substrate comprising a flex circuit.

Clause 25. The end effector of any one of clauses 19-24, the end effector comprising an array of at least four electrodes on the top side of the end effector, the array comprising the top electrodes of the first electrode pair and the second electrode pair, and the electrodes of the array being coplanar with each other.

Clause 26. The end effector of any one of clauses 19-25, further comprising: a support frame configured to move the first substrate portion, the second substrate portion, and the interlaced substrate into a predetermined shape.

Clause 27. The end effector of clause 26, the predetermined shape being planar.

Clause 28. The end effector of clause 26, the predetermined shape being selected from a group consisting essentially of a spheroid, conic or truncated cone.

Clause 29. The end effector of clause 26 or 27, the support frame comprising a plurality of longitudinally extending struts.

Clause 30. The end effector of any one of clauses 19-29, further comprising: a contiguous substrate comprising the first substrate portion and the second substrate portion.

Clause 31. The end effector of clause 30, the contiguous substrate further comprising: a first membrane facing the top side of the end effector such that a portion of the first membrane is exposed to ambient environment and a portion of the first membrane is traversed by the interlaced substrate; and a second membrane facing the bottom side of the end effector such that a portion of the second membrane is exposed to ambient environment and a portion of the second membrane is traversed by the interlaced substrate.

Clause 32. The end effector of clause 31, the contiguous substrate further comprising a nitinol support frame extending through the first substrate portion and/or the second substrate portion.

Clause 33. The end effector of clause 32, the frame comprising longitudinally extending struts, and the first membrane portion and/or the second membrane portion being disposed between the longitudinally extending struts.

Clause 34. The end effector of any one of clauses 19-29, further comprising: a support frame assembly comprising a first longitudinally extending strut and a second longitudinally extending strut such that the first substrate portion comprises the first longitudinally extending strut and the second substrate portion comprises the second longitudinally extending strut.

Clause 35. The end effector of clause 34, the first longitudinally extending strut being disposed between electrodes of the first electrode pair, and the second longitudinally extending strut being disposed between a electrodes of the second electrode pair.

Clause 36. The end effector of clause 34 or 35, further comprising: a third substrate portion; a fourth substrate portion; and respective openings between the second and third substrate portions and the third and fourth substrate portions, the interlaced substrate traversing the third substrate portion and the fourth substrate portion.

Clause 37. The end effector of clause 36, the interlaced substrate extending through the respective openings and traversing on the bottom side of the end effector across the third substrate portion and traversing on the top side of the end effector across the fourth substrate portion.

Clause 38. The end effector of clause 36 or 37, the support frame assembly further comprising a third longitudinally extending strut and a fourth longitudinally extending strut such that the third substrate portion comprises the third longitudinally extending strut and the fourth substrate portion comprises the fourth longitudinally extending strut.

Clause 39. The end effector of clause 38, the support frame assembly further comprising a first connecting strut and a second connecting strut such that the first connecting strut joins the first longitudinally extending strut and the third longitudinally extending strut and the second connecting strut joins the second longitudinally extending strut and the fourth longitudinally extending strut.

Clause 40. The end effector of clause 39, the first connecting strut being arcuate, and the second connecting strut being arcuate.

What is claimed is:

1. An end effector of a catheter, the end effector comprising:

a planar substrate extending along a longitudinal axis, the planar substrate comprising (i) openings therethrough, (ii) a frame comprising one or more struts extending along the longitudinal axis, a first membrane extending between the one or more struts on a first side of the planar substrate facing the first side of the end effector, and (iii) a second membrane extending between the one or more struts on a second side of the planar substrate facing the second side of the end effector; and an interlaced substrate traversing on a first side of the end effector across a first side of the planar substrate, extending through an opening through the planar substrate, and traversing on a second side of the end effector across a second side of the planar substrate opposite the first side of the planar substrate; and an electrode pair comprising an electrode affixed to the planar substrate and an electrode affixed to the interlaced substrate substantially opposite the electrode affixed to the planar substrate.

2. The end effector of claim 1, a portion of the first membrane being exposed to ambient environment, a portion of the first membrane being traversed by the interlaced substrate, a portion of the second membrane being exposed to ambient environment, and a portion of the second membrane being traversed by the interlaced substrate.

3. The end effector of claim 1, the electrodes of the electrode pair being exposed to ambient environment.

4. The end effector of claim 1, a first electrode of the electrode pair being configured to contact tissue, and a second electrode of the electrode pair being configured as a reference electrode to the first electrode.

5. The end effector of claim 1, in which a center of a first electrode of the electrode pair being substantially aligned with a center of a second electrode of the electrode pair.

6. The end effector of claim 1, the one or more struts comprising a pair of longitudinally extending struts that extend along the longitudinal axis; and the first membrane extending over each strut of the pair of longitudinally extending struts, and between the pair of longitudinally extending struts.

7. The end effector of claim 6, the electrode affixed to the planar substrate of the electrode pair being affixed to the first membrane and between the pair of longitudinally extending struts.

8. The end effector of claim 1, the end effector comprising an array of at least four electrodes on the first side of the end effector, the array comprising an electrode of the electrode pair that is on the first side of the end effector, and the electrodes of the array being coplanar with each other.

9. The end effector of claim 1, the end effector comprising an array of at least four electrodes on the first side of the end effector, the array comprising an electrode of the electrode pair that is on the first side of the end effector, and the electrodes of the array being coplanar with each other.

10. An end effector of a catheter, the end effector comprising:

a top side;

a bottom side opposite the top side;

a first substrate portion;

a second substrate portion;

an opening between the first and second substrate portions;

an interlaced substrate traversing on the top side of the end effector across the first substrate portion, extending through the opening, and traversing on a bottom side of the end effector across the second substrate portion;

a first electrode pair comprising a bottom electrode affixed to the first substrate portion on the bottom side of the end effector and a top electrode affixed to the interlaced substrate on the top side of the end effector, the top electrode being disposed substantially opposite the bottom electrode of the first electrode pair;

a second electrode pair comprising a top electrode affixed to the second substrate portion on the top side of the end effector and a bottom electrode affixed to the interlaced substrate on the bottom side of the end effector, the bottom electrode being disposed substantially opposite the top electrode of the second electrode pair; and a support frame configured to move the first substrate portion, the second substrate portion, and the interlaced substrate into a planar predetermined shape.

11. The end effector of claim 10, further comprising:

a contiguous substrate comprising the first substrate portion, the second substrate portion, and a nitinol support frame extending through the first substrate portion and/or the second substrate portion, the nitinol support frame comprising longitudinally extending struts, and the first substrate portion and/or the second substrate portion being disposed between the longitudinally extending struts;

a first membrane facing the top side of the end effector such that a portion of the first membrane is exposed to ambient environment and a portion of the first membrane is traversed by the interlaced substrate; and a second membrane facing the bottom side of the end effector such that a portion of the second membrane is exposed to ambient environment and a portion of the second membrane is traversed by the interlaced substrate.

12. An end effector of a catheter, the end effector comprising:

a planar substrate extending along a longitudinal axis, the planar substrate comprising (i) openings therethrough, (ii) a frame comprising a pair of longitudinally extending struts that extend along the longitudinal axis, and (iii) a membrane extending over each strut of the pair of longitudinally extending struts, and between the pair of longitudinally extending struts; and an interlaced substrate traversing on a first side of the end effector across a first side of the planar substrate, extending through an opening through the planar substrate, and traversing on a second side of the end effector across a second side of the planar substrate opposite the first side of the planar substrate; and an electrode pair comprising an electrode affixed to the planar substrate and an electrode affixed to the interlaced substrate substantially opposite the electrode affixed to the planar substrate.

13. The end effector of claim 12, a portion of the membrane being exposed to ambient environment, and a portion of the membrane being traversed by the interlaced substrate.

14. The end effector of claim 12, the electrodes of the electrode pair being exposed to ambient environment.

15. The end effector of claim 12, a first electrode of the electrode pair being configured to contact tissue, and a second electrode of the electrode pair being configured as a reference electrode to the first electrode.

16. The end effector of claim 12, in which a center of a first electrode of the electrode pair being substantially aligned with a center of a second electrode of the electrode pair.

17. The end effector of claim 12, the electrode affixed to the planar substrate of the electrode pair being affixed to the membrane and between the pair of longitudinally extending struts.

* * * * *